United States Patent [19]

Weyer et al.

[11] Patent Number: 5,276,165
[45] Date of Patent: Jan. 4, 1994

[54] PREPARATION OF N-SUBSTITUTED LACTAMS

[75] Inventors: Hans-Juergen Weyer, Mannheim; Rolf Fischer, Heidelberg, both of Fed. Rep. of Germany

[73] Assignee: BASF Aktiengesellschaft, Ludwigshafen, Fed. Rep. of Germany

[21] Appl. No.: 982,300

[22] Filed: Nov. 25, 1992

[30] Foreign Application Priority Data

Nov. 30, 1991 [DE] Fed. Rep. of Germany ....... 4139607

[51] Int. Cl.$^5$ ................. C07D 207/12; C07D 225/02; C07D 221/06
[52] U.S. Cl. ..................... 548/554; 540/451; 540/485; 540/532; 540/533; 540/538; 546/98; 546/216; 546/243; 548/450; 548/472; 548/543; 548/552
[58] Field of Search ............... 540/451, 485, 532, 533, 540/538; 546/243, 98, 216; 548/450, 471, 472, 543, 554, 552

[56] References Cited

U.S. PATENT DOCUMENTS

| | | | |
|---|---|---|---|
| 2,112,970 | 4/1938 | Millington | 260/127 |
| 2,192,523 | 3/1940 | Olin et al. | 260/583 |
| 3,109,005 | 10/1963 | Iklov et al. | 548/554 |
| 3,726,925 | 4/1973 | Fenton | 260/583 |
| 3,884,936 | 5/1975 | Hollstein | 548/554 |
| 4,014,933 | 3/1977 | Boettger et al. | 564/447 |
| 4,386,018 | 5/1983 | Merger et al. | 425/138 |
| 4,386,219 | 5/1983 | Merger et al. | 568/853 |
| 4,550,185 | 10/1985 | Mabry et al. | 549/508 |
| 4,609,636 | 9/1986 | Mabry et al. | 502/183 |
| 4,645,837 | 2/1987 | Laine et al. | 544/402 |
| 4,731,454 | 3/1988 | Otake et al. | 548/543 |
| 4,780,547 | 10/1988 | Zur Hausen et al. | 548/552 |
| 4,851,546 | 7/1989 | Graham et al. | 548/543 |
| 5,002,922 | 3/1991 | Irgang et al. | 564/480 |
| 5,157,127 | 10/1992 | Weyer et al. | 548/552 |

FOREIGN PATENT DOCUMENTS 2043294  5/1991  Canada .
44444    1/1982  European Pat. Off. .
147219   7/1985  European Pat. Off. .
0252242  1/1988  European Pat. Off. .
460474   12/1991 European Pat. Off. .
609245   2/1935  Fed. Rep. of Germany .
626923   3/1936  Fed. Rep. of Germany .
1953263  10/1969 Fed. Rep. of Germany .
2200600  1/1972  Fed. Rep. of Germany .
2321101  4/1973  Fed. Rep. of Germany .
3904083  8/1990  Fed. Rep. of Germany .
596006   12/1947 United Kingdom .
2000121  1/1979  United Kingdom .
2025399  1/1980  United Kingdom .

OTHER PUBLICATIONS

J. of Organometallic Chem., vol. 330, No. 3, Aug. 25, 1987, pp. 429–435.
J. of Amer. Chem. Society, vol. 107, 1985, pp. 361–369.
J. of Amer. Chem. Society, vol. 101, 1979, pp. 7429–7430.
J. of Amer. Chem. Society, vol. 100, 1978, pp. 348–350.
Isr. J. Chem., vol. 27, No. 3, 1986, pp. 267–275.
J. of Amer. Chem. Society, vol. 95, No. 9, May 2, 1973, pp. 3038–3039.
Chemical Reviews, vol. 70, No. 4, Aug. 1970.

Primary Examiner—Mukund Shah
Assistant Examiner—Y. N. Gupta
Attorney, Agent, or Firm—Keil & Weinkauf

[57] ABSTRACT

A process for the preparation of N-substituted lactams of the formula I

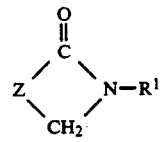

where
Z is $C_2$- to $C_{10}$-alkylene, $C_7$- to $C_{12}$-aralkylene, phenylene or naphthylene, and
$R^1$ is $C_1$- to $C_{20}$-alkyl, $C_6$- to $C_{10}$-aryl or $C_7$- to $C_{12}$-aralkyl, by hydrogenating a compound of the formula II (Abstract continued on next page.)

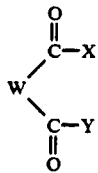 (II)

where
W is $C_2$- to $C_{10}$-alkylene, $C_2$- to $C_{10}$-alkenylene, $C_7$- to $C_{12}$-aralkylene, phenylene or naphthylene, and
X and Y together form an oxa or imido bridge of the formula

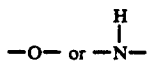

or alternatively are identical or different and are hydroxyl, $C_1$- to $C_{20}$-alkoxy, $C_6$- to $C_{10}$-aryloxy or $C_7$- to $C_{12}$-aralkoxy, and, if X and Y are different, Y, in addition to the abovementioned meanings, may also be hydrogen, at superatmospheric pressure and at elevated temperature in the presence of a catalyst and in the presence of an amine, which comprises using a secondary and/or tertiary amine of the formula III $NH_nR_{3-n}{}^1$ where $R^1$ is as defined above and n is 0 or 1, or a mixture of a secondary and/or teritary amine of this type with a primary amine of the formula IV $R^1-NH_2$ (IV)

as the starting material, and carrying out the reaction with addition of water and/or ammonia.

7 Claims, No Drawings

PREPARATION OF N-SUBSTITUTED LACTAMS

The present invention relates to a process for the preparation of N-substituted lactams of the formula

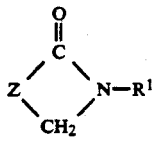
(I)

where
Z is $C_2$- to $C_{10}$-alkylene, $C_7$- to $C_{12}$-aralkylene, phenylene or naphthylene, and
$R^1$ is $C_1$- to $C_{20}$-alkyl, $C_6$- to $C_{10}$-aryl or $C_7$- to $C_{12}$-aralkyl,
by hydrogenating a compound of the formula II

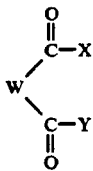
(II)

where
W is $C_2$- to $C_{10}$-alkylene, $C_2$- to $C_{10}$-alkenylene, $C_7$- to $C_{12}$-aralkylene, phenylene or naphthylene, and
X and Y together form an oxa or imido bridge of the formula

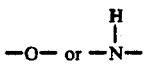

or alternatively are identical or different and are hydroxyl, $C_1$- to $C_{20}$-alkoxy, $C_6$- to $C_{10}$-aryloxy or $C_7$- to $C_{12}$-aralkoxy, and, if X and Y are different, Y, in addition to the abovementioned meanings, may also be hydrogen,
at superatmospheric pressure and at elevated temperature in the presence of a catalyst and in the presence of an amine.

Lactams can be prepared in various ways. Lactams having a relatively large number of ring atoms, such as ε-caprolactam, are obtained, for example, by Beckmann rearrangement of the corresponding oxime. To prepare N-substituted lactams, the lactams obtained in this way must be N-alkylated in a second step, for example by reaction with an alcohol. N-substituted lactams having a smaller ring size are generally obtained by reacting the corresponding lactone with a primary amine.

Recent patent applications relate to the preparation of N-substituted lactams by catalytic hydrogenation of substituted dicarboxylic acid imides or monoamides. These must first be prepared by reacting dicarboxylic acid derivatives with primary amines. However, it is also known to catalytically hydrogenate dicarboxylic acids and their derivatives in the presence of primary amines to give N-substituted lactams (cf. European Patent Application 91108503).

U.S. Application No. 4,731,454 describes the preparation of N-methylpyrrolidone (NMP) by hydrogenating N-methylsuccinimide on a cobalt/rhenium/molybdenum catalyst. U.S. Application No. 3,109,005 discloses a process for the preparation of NMP by hydrogenating maleic anhydride (MAA)/methylamine mixtures on a Raney nickel catalyst. At reaction times of 10 hours, NMP yields of 70% are achieved in this process. According to the process of DE-A 22 00 600, NMP is obtained in a yield of 44% under the most favorable conditions by hydrogenating MAA/methylamine mixtures on palladium supported catalysts.

All these preparation processes have the disadvantage that they require pure primary amines. However, primary amines, in particular in large-scale industrial processes, are not produced in pure forms, but instead as mixtures of primary, secondary and tertiary amines. For the preparation of N-substituted lactams by hydrogenating amination of dicarboxylic acids or dicarboxylic acid derivatives, such as dicarboxylic anhydrides or esters, it has therefore hitherto been necessary to separate the primary amines required from tertiary and secondary amines in a complex purification process. This requirement makes these processes considerably more expensive.

It is an object of the present invention to provide an economical process which enables secondary and tertiary amines to be used as an amine source in the hydrogenating amination of dicarboxylic acids, dicarboxylic acid derivatives and/or formylcarboxylic acids and/or derivatives thereof to give N-substituted lactams.

We have found that this object is achieved by a process for the preparation of N-substituted lactams of the formula I

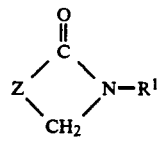
(I)

where
Z is $C_2$- to $C_{10}$-alkylene, $C_7$- to $C_{12}$-aralkylene, phenylene or naphthylene, and
$R^1$ is $C_1$- to $C_{20}$-alkyl, $C_6$- to $C_{10}$-aryl or $C_7$- to $C_{12}$-aralkyl,
by hydrogenating a compound of the formula II

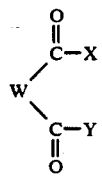
(II)

where
W is $C_2$- to $C_{10}$-alkylene, $C_2$- to $C_{10}$-alkenylene, $C_7$- to $C_{12}$-aralkylene, phenylene or naphthylene, and
X and Y together form an oxa or imido bridge of the formula

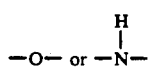

or alternatively are identical or different and are hydroxyl, $C_1$- to $C_{20}$-alkoxy, $C_6$- to $C_{10}$-aryloxy or $C_7$- to $C_{12}$-aralkoxy, and, if X and Y are different, Y, in addition to the abovementioned meanings, may also be hydrogen, at superatmospheric pressure and at elevated temperature in the presence of a catalyst and in the presence of an amine, which comprises using a secondary and/or tertiary amine of the formula III

 (III)

where $R^1$ is as defined above and n is 0 or 1, or a mixture of a secondary and/or tertiary amine of this type with a primary amine of the formula IV

 (IV)

as the starting material, and carrying out the reaction with addition of water and/or ammonia.

The novel process is thus capable of using both secondary and tertiary amines or mixtures of these amines as an amine source in the preparation of N-substituted lactams. However, particular preference is given to the amine mixtures obtained directly on reductive amination of alcohols, for example by the processes of DE-A 19 53 263 and U.S. Application No. 5,002,922. The use of amine mixtures of this type, which contain primary, secondary and tertiary amines, has the advantage that additional purification steps for the isolation of certain amine species from the reductive amination amine mixture are no longer necessary. The content of the individual primary, secondary and tertiary amine components in amine mixtures of this type is generally unimportant for the process according to the invention, ie. it is possible to use both amine mixtures containing predominantly primary and only little secondary and/or tertiary amines or amine mixtures which contain no primary amines.

The amines are usually employed in an amine: compound II molar ratio, with respect to the dicarboxylic acids, dicarboxylic acid derivatives, formylcarboxylic acids and/or formylcarboxylic acid derivatives II, of from 0.5:1 to 5:1, preferably from 0.8:1 to 2:1, particularly preferably from 1:1 to 1.5:1. It is of course possible to use higher or lower molar ratios, but these are generally less preferred for economic reasons. If amine mixtures are used in the process according to the invention, the total number of moles of the primary, secondary and tertiary amine components present in the amine mixture is used to calculate the amine: compound II molar ratio.

It is important to the success of the process according to the invention that water and/or ammonia is added to the reaction mixture. The water should be in freely available form in the reaction mixture, since it presumably participates in the reaction. In general, the water is added in an amount, with respect to the amines present in the reaction mixture, of from 0.1 to 100 mol, preferably from 1 to 50 mol, in particular from 5 to 20 mol, per mole of amine or amines.

The use of ammonia in place of water may be particularly advantageous in the process according to the invention, in particular if the reaction of the dicarboxylic acids or dicarboxylic acid derivatives is to be carried out in a non-aqueous medium. An anhydrous procedure may be expedient, in particular if the reactants are not sufficiently soluble in water. The ammonia is generally employed in an amount of from 0.1 to 100 mol, preferably from 1 to 50 mol, particularly advantageously from 1 to 10 mol, per mole of amine or amines.

It is of course also possible and advantageous to use aqueous ammonia solutions in the process according to the invention. With respect to optimum metering of the water and/or ammonia within the stated ranges, it should be stated that the latter can advantageously be determined for the particular amine mixture used in simple preliminary experiments.

The reaction according to the invention can be carried out in the presence or absence of a solvent. As solvent, virtually any solvent can be used which is inert under the reaction conditions, for example water, aliphatic and aromatic hydrocarbons, such as pentane, hexane, heptane, octane, benzene, toluene and xylene, ethers, such as diethyl ether, diisopropyl ether, methyl tert-butyl ether, dioxane or tetrahydrofuran, or mixtures of these solvents. N-substituted lactams, in particular the lactam formed as product in the reaction concerned, can also advantageously be used as the solvent. The particularly preferred solvent is water. The compounds II are generally mixed with the solvent in a compound II: solvent molar ratio of from 1:1 to 1:100, usually from 1:5 to 1:50.

The hydrogen required for the reaction can be added to the reaction mixture in stoichiometric amounts; it is expedient to use an excess of hydrogen. The extent of the hydrogen excess used in the process according to the invention is not crucial, since the unconsumed hydrogen can be recycled into the reaction. The hydrogen can be fed to the reaction in pure form or diluted with an inert gas, such as nitrogen or argon; undiluted hydrogen is preferred.

The hydrogenating reaction of the compounds II with the secondary or tertiary amines or the amine mixtures containing these amines is usually carried out at from 100° to 350° C., preferably at from 150° to 300° C., and at from 50 to 350 bar, in particular at from 100 to 300 bar. The pressure desired in the reactor at the respective reaction temperatures can expediently be set by injecting hydrogen into the reactor. The sequence of addition of the reactants into the reactor is generally unimportant.

The reaction can be carried out batchwise, for example in a stirred autoclave, but is preferably carried out continuously, for example in a tubular reactor or tube-bundle reactor, it being possible to dissipate the heat of hydrogenation by external or internal cooling. A further way of regulating the reaction temperature is to recycle some of the hydrogenation product and the excess hydrogen after prior cooling, for example in a heat exchanger.

The hydrogenating reaction can be controlled in such a manner that a certain pressure and temperature range is maintained during the entire reaction. However, in particular in the case of throughput of relatively large amounts, it may be beneficial for the selectivity and service life of the catalyst to carry out the reaction at different pressure and temperature levels, for example by first partially hydrogenating the reaction mixture in a first reactor at from 100° to 220° C. and at from 50 to 200 bar and subsequently passing the hydrogenation product into the next reactor without work-up and then completing the hydrogenating reaction at, for example, from 220° to 300° C. and at from 200 to 350 bar.

The hydrogenation products obtained in this way may under certain circumstances contain small amounts of byproducts, such as N-substituted dicarboximides, dicarboxylic diamides, dicarboxylic monoamides, and the like, in addition to the desired N-substituted lactams. These hydrogenation products can be worked up by extraction or advantageously by distillation. The partially hydrogenated byproducts separated off in this way can, since they can be hydrogenated to give N-substituted lactams, be recycled into the hydrogenation zone in order to achieve complete conversion.

The hydrogenating reaction can be carried out using conventional heterogeneous hydrogenation catalysts, in particular those containing, in their active material, at least one element from the first, seventh or eighth subgroup of the Periodic Table of the Elements, in particular at least one of the elements iron, rhenium, ruthenium, cobalt, rhodium, nickel, palladium, platinum, copper and silver. Examples of other elements which may be present in the catalytically active material are chromium, molybdenum, tungsten and/or manganese. The catalysts may be employed in finely divided form, for example as Raney nickel, Raney cobalt, platinum sponge, palladium sponge or iron carbonyl powder, or alternatively in the form of turnings, meshes or other structures having a large surface area. It is also advantageous to use supported catalysts containing the catalytically active metals deposited on an inert support material, such as activated charcoal, silicon dioxide, aluminum oxide, titanium dioxide, zirconium dioxide, a silicate, such as steatite or pumice, barium sulfate or calcium carbonate. Examples of such catalysts include palladium on activated charcoal, platinum on activated charcoal, palladium on barium sulfate and palladium on calcium carbonate.

Precipitation catalysts may likewise be used in the process according to the invention with very good results. For the purposes of the present invention, precipitation catalysts are taken to mean catalysts whose catalytically active components are precipitated from the solutions of their salts, for example their nitrates, with the aid of a precipitant, for example by means of an alkali metal hydroxide solution, alkaline earth metal hydroxide solution, alkali metal carbonate solution or alkaline earth metal carbonate solution, and are subsequently dried and calcined. The calcined catalyst compositions obtained in this way, which contain the catalytically active components principally in oxidic form, may if desired be shaped with the aid of a shaping assistant, such as graphite, stearic acid or phosphoric acid. Before use as catalysts, the catalyst moldings obtained in this way are generally activated by reduction in a stream of hydrogen at elevated temperature, during which the catalyst components which can be reduced by means of hydrogen are reduced, in general mostly to the corresponding metals. These precipitation catalysts can be prepared in compact form, ie. without support materials, but may advantageously also be obtained as supported catalysts. For this purpose, the catalytically 15 active components can be precipitated, for example, on a preprecipitated support material or precipitated together with the support material in a coprecipitation from a solution of the corresponding salts. Examples of particularly suitable support materials for precipitation catalysts of this type are silicon dioxide, aluminum oxides, titanium dioxides, zirconium dioxide and silicates.

In addition to the abovementioned catalysts, catalysts which are particularly preferred in the process according to the invention are those described in U.S. Application No. 4,731,454, DE-A 23 21 101, DE-A 39 04 083, EP-A 44 444 and EP-A 147 219.

The catalysts can be used in suspended form in the process according to the invention, but preference is given to a fixed-bed arrangement of the catalyst, through which the starting materials can be passed upward or downward.

The starting material for the preparation of N-substituted lactams by the process according to the invention are the compounds of the formula II

where
W is $C_2$- to $C_{10}$-alkylene, $C_2$- to $C_{10}$-alkenylene, $C_7$- to $C_{12}$-aralkylene, phenylene or naphthylene, and
X and Y together form an oxa or imido bridge of the formula

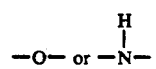

or alternatively are identical or different and are hydroxyl, $C_1$- to $C_{20}$-alkoxy, $C_6$- to $C_{10}$-aryloxy or $C_7$- to $C_{10}$-aralkoxy, and, if X and Y are different, Y, in addition to the abovementioned meanings, may also be hydrogen.

Preference is given to compounds II where Z is $C_2$- to $C_4$-alkylene, $C_2$- to $C_4$-alkenylene or phenylene. Alkylene and alkenylene Z may be straight-chain, branched or cyclic. Z is particularly preferably ethylene, ethenylene, 1,3-propylene, 1,2-propylene, 1-propen-3-yl, 1-propen-2-yl, 1,4-butylene or 1,2-phenylene.

X and Y in the starting material of the formula II may be identical or different. For example, X and Y may together form an oxa or imido bridge, so the compounds II are cyclic dicarboxylic anhydrides or dicarboximides. However, the starting compounds II may also be open-chain dicarboxylic acids if X and Y are hydroxyl, or dicarboxylic acid diesters if X and Y are alkoxy, aryloxy and/or aralkoxy.

It is of course also possible successfully to use starting compounds II in the process according to the invention where X and Y are different and are one of the abovementioned functional groups. Examples of such compounds are dicarboxylic acid monoesters, formylcarboxylic acids and formylcarboxylic acid esters. The use of formylcarboxylic acids of the formula IIa

is of course equivalent to the use of the lactols thereof of the formula V

since the formylcarboxylic acids IIa are in equilibrium with their lactols V in the presence of water.

The same applies to mixtures of the various dicarboxylic acid derivatives. Nevertheless, preference is generally given to starting compounds II where X and Y are identical. Likewise, preferred formylcarboxylic acid esters as starting materials are those which can be prepared inexpensively by hydroformylation of the corresponding alkenecarboxylic acid esters, for example by hydroformylation of acrylates or methacrylates by the process of EP-A 173 226.

X and Y are preferably hydroxyl, $C_1$- to $C_{10}$-alkoxy, in particular $C_1$- to $C_4$-alkoxy, such as methoxy, ethoxy, propoxy, isopropoxy or butoxy, phenoxy or benzyloxy. Y is additionally preferably hydrogen.

Particularly preferred starting materials are maleic acid, maleic anhydride, maleimide, $C_1$- to $C_4$-dialkyl maleate, succinic acid, succinic anhydride, succinimide, $C_1$- to $C_4$-dialkyl succinate, adipic acid, $C_1$- to $C_4$-dialkyl adipate, phthalic acid, phthalic anhydride, phthalimide, $C_1$- to $C_{10}$-dialkyl phthalate, $C_1$- to $C_4$-monoalkyl maleate, $C_1$- to $C_4$-monoalkyl succinate, $C_1$- to $C_4$-monoalkyl adipate, $C_1$- to $C_4$-monoalkyl phthalate, $C_1$- to $C_4$-esters of 3-formylpropionic acid and $C_1$- to $C_4$-esters of 3-formyl-2-methylpropionic acid.

The starting compounds II are large-volume industrial products and are available in large amounts. Maleic anhydride can be prepared by oxidizing aromatic compounds, butene or butane by the methods outlined in K. Weissermel, H.-J. Arpe, Industrielle organische Chemie, 2nd Edition, pages 343 to 349, Verlag Chemie, Weinheim, 1978. Hydrolysis or alcoholysis of maleic anhydride gives maleic acid or monoesters of maleic acid. Diesters of maleic acid can be obtained therefrom in a conventional esterification reaction. Succinic acid and the succinic acid derivatives mentioned can be obtained from maleic acid and the corresponding maleic acid derivatives by hydrogenation of the double bond. Cyclic dicarboximides can be prepared by the process of Chem. Rev. 70 (1970) 439. Adipic acid is prepared on an industrial scale by the oxidation of cyclohexanol/cyclohexanone (cf. Weissermel, Arpe: pages 227 to 229). Esters of adipic acid can be produced therefrom by conventional esterification processes. Phthalic anhydride is produced on an industrial scale by the oxidation of xylene and converted to phthalic acid esters, likewise on an industrial scale, by conventional processes (cf. Weissermel, Arpe: pages 359 to 364). Hydrolysis of phthalic anhydride gives phthalic acid, and alcoholysis gives monoesters of phthalic acid.

The process according to the invention for the preparation of N-substituted lactams can use secondary and tertiary amines of the formula III

  (III)

as an amine source, where $R^1$ is $C_2$- to $C_{10}$-alkyl, $C_6$- to $C_{10}$-aryl and/or $C_7$- to $C_{12}$-aralkyl, and n is 0 or 1. The aliphatic radicals $R^1$ may be straight-chain, branched or cyclic. $R^1$ is particularly preferably methyl, ethyl, propyl or n-butyl. As stated above, these amines may be produced by hydrogenating amination of the corresponding alcohols and ketones.

In the reaction according to the invention, the carboxylic acid compounds II and the secondary and tertiary amines III used according to the invention give, under the reaction conditions used, the corresponding dicarboxylic acid diamides, dicarboxylic acid monoamides, formylcarboxylic acid amides, formylcarboxylic acid ammonium salts, dicarboxylic acid mono- and diammonium salts, dicarboxylic acid monoester monoamides, dicarboxylic acid monoamide monoammonium salts, and the like, as intermediates; these smoothly react further to give the desired lactams. It therefore goes without saying that these intermediates can be employed in place of the abovementioned starting materials and that their use is equivalent to the use of the abovementioned starting materials.

The N-substituted lactams which can be prepared by the process according to the invention have a wide range of uses, for example as polar solvents or extractants. For example, N-methylpyrrolidone is used as a solvent for polymers, such as polyurethanes, polyimides, polyamides and polyarylene sulfides, as an extractant for acetylene, butadiene and aromatic hydrocarbons, and as a solvent for chemical reactions (cf. in this respect: Ullmanns Encyklopädie der technischen Chemie, 4th Edition, Volume 19, pages 641 to 642, Verlag Chemie, Weinheim, 1980).

EXAMPLES

In the examples below, catalysts which had the following composition in the unreduced state were used:

Catalyst A (according to EP-A 44 444)

50% by weight of Cu, calculated as CuO
50% by weight of Al, calculated as $Al_2O_3$ Catalyst B (according to DE-A 39 04 083)

63.4 % by weight of Co, calculated as CoO
18.1 % by weight of Cu, calculated as CuO
6.8 % by weight of Mn, calculated as $Mn_2O_3$
3.1 % by weight of Mo, calculated as $MoO_3$
0.15% by weight of Na, calculated as $Na_2O$
3.3 % by weight of phosphoric acid, calculated as $H_3PO_4$

EXAMPLE 1

9.8 g (0.1 mol) of MAA, 100 g of water, 0.4 mol of amine and 10 g of catalyst A were introduced as suspension catalyst into an autoclave fitted with a gas distribution stirrer. The autoclave was subsequently heated to 225° C., and hydrogen was injected into the autoclave at a pressure of 200 bar. When take-up of hydrogen was no longer observed, the reaction was terminated and the autoclave contents analyzed by gas chromatography. The yields of NMP shown in Table 1 were achieved for the amines employed in the individual reactions.

TABLE 1

| Amine employed | NMP yield (based on MAA employed) |
|---|---|
| Dimethylamine | 53% |
| Trimethylamine | 41% |
| Monomethylamine | 38% |

EXAMPLE 2

In a heatable tubular reactor (length 200 mm, internal diameter 16 mm) containing 38 g of catalyst B arranged in a fixed bed, the reactants were passed over the catalyst and filtered in a downward direction at 250° C. and an overall pressure of 200 bar. The reaction products were cooled to room temperature, decompressed and separated into their gaseous and liquid constituents in a gas/liquid separator. The composition of the product mixture obtained was determined by gas chromatography.

In this reaction, the space/velocity was 0.15 kg (1.5 mol) of MAA, 0.06 kg (0.94 mol) of monomethylamine, 0.02 kg (0.44 mol) of dimethylamine, 0.01 kg (0.17 mol) of trimethylamine and 0.55 kg of water per kg of catalyst, with 2500 l (s.t.p.) h of hydrogen being introduced per kg of catalyst.

Under these conditions, a mean NMP yield of 89%, based on the MAA employed, was achieved over a running time of 9 hours. If, by contrast, only 0.06 kg of monomethylamine were passed over the catalyst under the same reaction conditions, an NMP yield of only 77%, based on the MAA employed, was obtained.

EXAMPLE 3

5 g (0.05 mol) of MAA, 100 g of tetrahydrofuran, 9 g (0.06 mol) of dicyclohexylamine, 4 g of ammonia and 10 g of catalyst B were introduced into an autoclave fitted with a gas-distribution stirrer. The autoclave was subsequently heated to 225° C., and hydrogen was injected into the autoclave at a pressure of 200 bar. When take-up of hydrogen was no longer observed, the reaction was terminated. Analysis of the reaction mixture by gas chromatography gave a yield of 8.8% of N-cyclohexylpyrrolidone.

We claim:

1. A process for the preparation of N-substituted lactams of the formula I

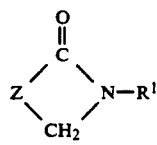

where

Z is $C_2$- to $C_{10}$-alkylene, $C_7$- to $C_{12}$-aralkylene, phenylene or naphthylene, and $R^1$ is $C_1$- to $C_{20}$-alkyl, $C_6$- to $C_{10}$-aryl or $C_7$- to $C_{12}$-aralkyl, by hydrogenating a compound of the formula II

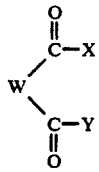

where

W is $C_2$- to $C_{10}$-alkylene, $C_2$- to $C_{10}$-alkenylene, $C_7$- to $C_{12}$-aralkylene, phenylene or naphthylene, and X and Y together form an oxa or imido bridge of the formula

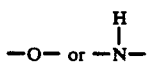

or alternatively are identical or different and are hydroxyl, $C_1$- to $C_{20}$-alkoxy, $C_6$- to $C_{10}$-aryloxy and/or $C_7$- to $C_{12}$-aralkoxy, and, if X and Y are different, Y, in addition tot he abovementioned meanings, may also be hydrogen, at superatmospheric pressure and at elevated temperature in the presence of a catalyst and in the presence of an amine, which comprises using a secondary and/or tertiary amine of the formula III

where $R^1$ is as defined above and n is 0 or 1, or a mixture of a secondary and/or tertiary amine of this type with a primary amine of the formula IV

as the starting material, and carrying out the reaction with addition of water and/or ammonia.

2. A process as claimed in claim 1, wherein the reaction is carried out in the presence of at least 1 mol of water per mole of amine.

3. A process as claimed in claim 1, wherein the reaction is carried out in the presence of at least 1 mol of ammonia per mole of amine.

4. A process as claimed in claim 1, wherein the reaction is carried out in a solvent.

5. A process as claimed in claim 1, wherein the reaction is carried out in water as solvent.

6. A process as claimed in claim 1, wherein the reaction is carried out at from 100° to 300° C. and at from 50 to 350 bar.

7. A process as claimed in claim 1, wherein a catalyst is used whose active component contains at least one element of the first, seventh or eighth sub-group of the Periodic Table of the Elements.

* * * * *

UNITED STATES PATENT AND TRADEMARK OFFICE
CERTIFICATE OF CORRECTION

PATENT NO. : 5,276,165
DATED : January 4, 1994
INVENTOR(S) : WEYER et al.

It is certified that error appears in the above-indentified patent and that said Letters Patent is hereby corrected as shown below:

On title page, item [57] Abstract, the
formula "$NH_nR_{3-n}^1$" should be —$NH_nR^1{}_{3-n}$—

Claim 1, column 10, line 30, the formula "$NH_nR_{3-n}^1$" should be —$NH_nR^1{}_{3-n}$—

Signed and Sealed this

Eighth Day of November, 1994

Attest:

BRUCE LEHMAN

Attesting Officer

Commissioner of Patents and Trademarks